United States Patent
Engström

(10) Patent No.: US 9,863,850 B2
(45) Date of Patent: Jan. 9, 2018

(54) METHOD AND SYSTEM FOR MEASURING THE MASS FLOW BY MEANS OF DILUTION OF AN EXHAUST GAS FROM INTERNAL COMBUSTION

(71) Applicant: Rototest International AB, Rönninge (SE)

(72) Inventor: Christian Engström, Tyresö (SE)

(73) Assignee: Rototest International AB, Rönninge (SE)

( * ) Notice: Subject to any disclaimer, the term of this patent is extended or adjusted under 35 U.S.C. 154(b) by 110 days.

(21) Appl. No.: 14/370,196

(22) PCT Filed: Dec. 28, 2012

(86) PCT No.: PCT/SE2012/051506
§ 371 (c)(1),
(2) Date: Jul. 1, 2014

(87) PCT Pub. No.: WO2013/103314
PCT Pub. Date: Jul. 11, 2013

(65) Prior Publication Data
US 2014/0331980 A1    Nov. 13, 2014

(30) Foreign Application Priority Data
Jan. 2, 2012   (SE) ..................... 1250001

(51) Int. Cl.
*G01F 1/704* (2006.01)
*G01M 15/10* (2006.01)
(Continued)

(52) U.S. Cl.
CPC ............ *G01M 15/102* (2013.01); *G01F 1/00* (2013.01); *G01F 1/74* (2013.01); *G01F 1/86* (2013.01);
(Continued)

(58) Field of Classification Search
CPC .......... G01M 15/102; G01F 1/00; G01F 1/74; G01F 1/86; G01F 1/704; G01N 1/2252;
(Continued)

(56) References Cited

U.S. PATENT DOCUMENTS 3,881,351 A * 5/1975 Prachar ................... G01F 1/704
250/356.1
4,149,376 A * 4/1979 Masaki ..................... F01N 3/22
60/276
(Continued)

FOREIGN PATENT DOCUMENTS

DE  10 2008 044 041 A1   5/2010
EP       1 391 700 A1     2/2004
JP       9-318572 A      12/1997

*Primary Examiner* — Hai Huynh
*Assistant Examiner* — Gonzalo Laguarda
(74) *Attorney, Agent, or Firm* — Blank Rome LLP

(57) ABSTRACT

The present invention relates to a method for measuring the content of at least one compound in an exhaust gas stream resulting from internal combustion. A first relative proportion of a first compound in the exhaust gas stream is measured by means of a first sensor, and a defined flow of a first gas is added to said exhaust gas stream downstream said first sensor. A second relative proportion of said first compound in the combined stream of said exhaust gas stream and said added gas is measured by means of a second sensor, and a mass flow of said first compound in said exhaust gas stream resulting from said combustion in said internal combustion is determined by means of said first and second relative proportions and said defined flow of said first gas. The invention also relates to a system and vehicle dynamometer.

25 Claims, 4 Drawing Sheets

(51) Int. Cl.
*G01F 1/86* (2006.01)
*G01F 1/00* (2006.01)
*G01F 1/74* (2006.01)
*G01N 1/22* (2006.01)
*G01N 33/00* (2006.01)

(52) U.S. Cl.
CPC ....... *G01N 1/2252* (2013.01); *G01N 33/0036* (2013.01)

(58) Field of Classification Search
CPC ... G01N 33/0036; F01N 3/22; F02D 41/1454; F02D 41/1455; F02D 41/1456; F02D 41/1441
USPC .......... 60/289, 304, 307, 308; 123/691, 692, 123/699; 701/103, 109
See application file for complete search history.

(56) References Cited

U.S. PATENT DOCUMENTS

| | | | |
|---|---|---|---|
| 6,085,582 A | | 7/2000 | Tripathi et al. |
| 6,112,575 A | * | 9/2000 | Cocconi .............. G01M 15/106 73/114.74 |
| 7,263,823 B2 | * | 9/2007 | Andrews ............... F01N 3/0807 60/274 |
| 2002/0166390 A1 | | 11/2002 | Graze |

\* cited by examiner

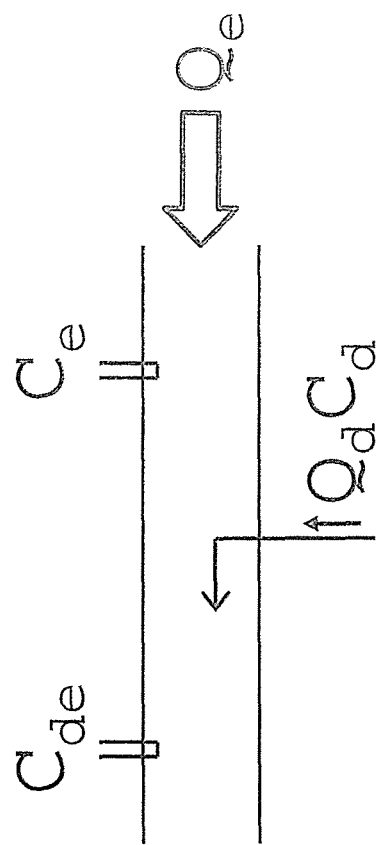
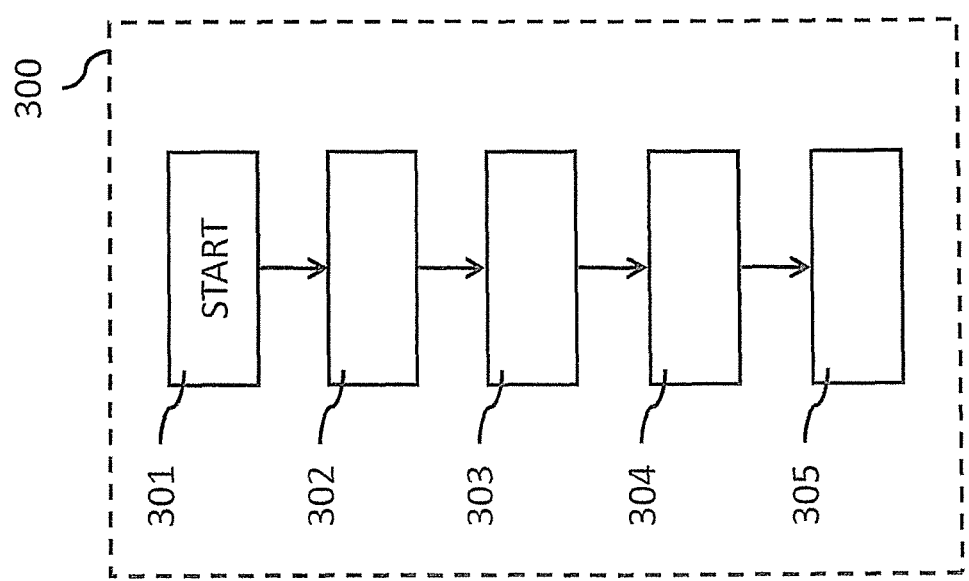

METHOD AND SYSTEM FOR MEASURING THE MASS FLOW BY MEANS OF DILUTION OF AN EXHAUST GAS FROM INTERNAL COMBUSTION

FIELD OF THE INVENTION

The present invention relates to methods and systems for testing vehicles, and in particular to a method and system for testing exhaust emissions and/or fuel consumption of a vehicle, where a measurement apparatus is connected to the vehicle tail pipe.

BACKGROUND OF THE INVENTION

Increasing governmental concerns regarding pollution and air quality, in particular in urban areas, has generated various exhaust standards and regulations in many different jurisdictions.

For example, there exist emission standards in e.g. North America, Europe and Asia, where the emission standards define acceptable limits for e.g. vehicle exhaust emissions.

For example, emissions of nitric oxides ($NO_x$) hydrocarbons (HC), carbon monoxide (CO) are regulated in such standards, and compliance to the standards usually is determined by running the vehicle engine at a standardized test cycle.

When evaluating vehicle performance by means of such test cycles, in general, apart from exhaust emissions, fuel consumption is also measured. However, measurement apparatus for performing such measurements are often complex and expensive which, in turn, limits use of such measurement apparatus in various other situations.

For example, there exist various occasions when vehicles are being tested where fuel consumption measurements and/or exhaust emission measurements is of interest. For example, vehicle after market companies, such as vehicle diagnostic and service companies, often are interested in the vehicle current status in respect of fuel consumption and/or exhaust emissions. As another example, during vehicle drive train development, by vehicle manufacturers or universities or institutes, there also often exist various situations when measurement results in regard of fuel consumption and/or exhaust emissions is of particular interest.

Consequently, there exists a need for a system and method for testing fuel consumption and/or exhaust emissions that is favourable e.g. from a cost and/or complexity perspective.

Aim and Most Important Features of the Invention

It is an object of this invention to provide a method and a device for measuring at least one compound in an exhaust gas stream resulting from combustion in an internal combustion engine that overcome the problems of the background art.

In particular, the present invention relates to a method for measuring the content of at least one compound in an exhaust gas stream resulting from internal combustion, said method including:
  by means of a first sensor, measuring a first relative proportion of a first compound in the exhaust gas stream,
  downstream said first sensor, adding a defined flow of a first gas to said exhaust gas stream,
  by means of a second sensor, measuring a second relative proportion of said first compound in the combined stream of said exhaust gas stream and said added gas, and
  determining a mass flow of said first compound in said exhaust gas stream resulting from said combustion in said internal combustion engine by means of said first and second relative proportions and said defined flow of said first gas.

This has the advantage that a device for measuring a mass flow, i.e. an absolute content of a compound occurring in an exhaust gas stream with high accuracy can be obtained using low-cost sensors and components. Consequently, the present invention provides for a method that allows inexpensive, high-accuracy measurements using a considerably less complex and expensive solution as compared to traditional complicated and expensive flow sensors. The said first and second sensors cannot individually measure flow of the exhaust gas stream, but instead the flow is determined using two sensors and addition of a defined, i.e. known flow of a dilution gas.

Consequently, the mass flow of the first compound can be determined by means of sensors that are capable of determining a relative proportion of a compound, but which sensors are not capable of measuring a flow. Hence, the present invention allows determination of a flow without use of any actual flow meters.

Furthermore, by adding a defined, i.e. controlled, flow of dilution gas by means such that use of flow meters for delivering the flow of dilution gas is not required, the invention has the advantage that no flow meter is required to measure the flow of the dilution gas either.

For example, said defined (controlled) flow can be added by a controlled throttling, such as by means of a critical nozzle, or by drawing a defined amount of dilution gas by means of a constant volume pump, where the flow drawn by the constant volume pump is then added to the exhaust gas flow.

Furthermore, the addition of a controlled flow of dilution gas has the advantage that the dilution gas flow will be the same irrespective of changes in the exhaust gas flow, and hence will not vary just because the exhaust gas flow varies.

Still, during measurements the added dilution gas flow can be arranged to be varied, e.g. based on measurement results, to set the dilution gas to a flow that based on the measurements is suitable for the current exhaust gas flow. These variations, however, are controlled and the dilution gas flow still does not does not vary under the influence of the exhaust gas flow, but only as set by the measurement system.

Measurements can be performed by connecting a measurement device to the vehicle exhaust system tail pipe. The connection is preferably an airtight connection. This has the advantage that measurements can be performed in a simple manner with substantially no manipulation of the vehicle. This also allows for quick and easy set-up of the measurement device, and due to the relatively few components needed for performing measurements, the measurement device according to the present invention can be made portable and easy to transport between different measurement locations.

According to one embodiment, the mass flow of the exhaust gas stream is determined.

BRIEF DESCRIPTION OF THE DRAWINGS

The invention will now be described more in detail with reference to the drawings, wherein:

FIG. 3 shows an exemplary method according to the present invention.

FIG. 5 illustrates flows occurring in a system according to the present invention.

DETAILED DESCRIPTION OF PREFERRED EMBODIMENTS

Figure 1:
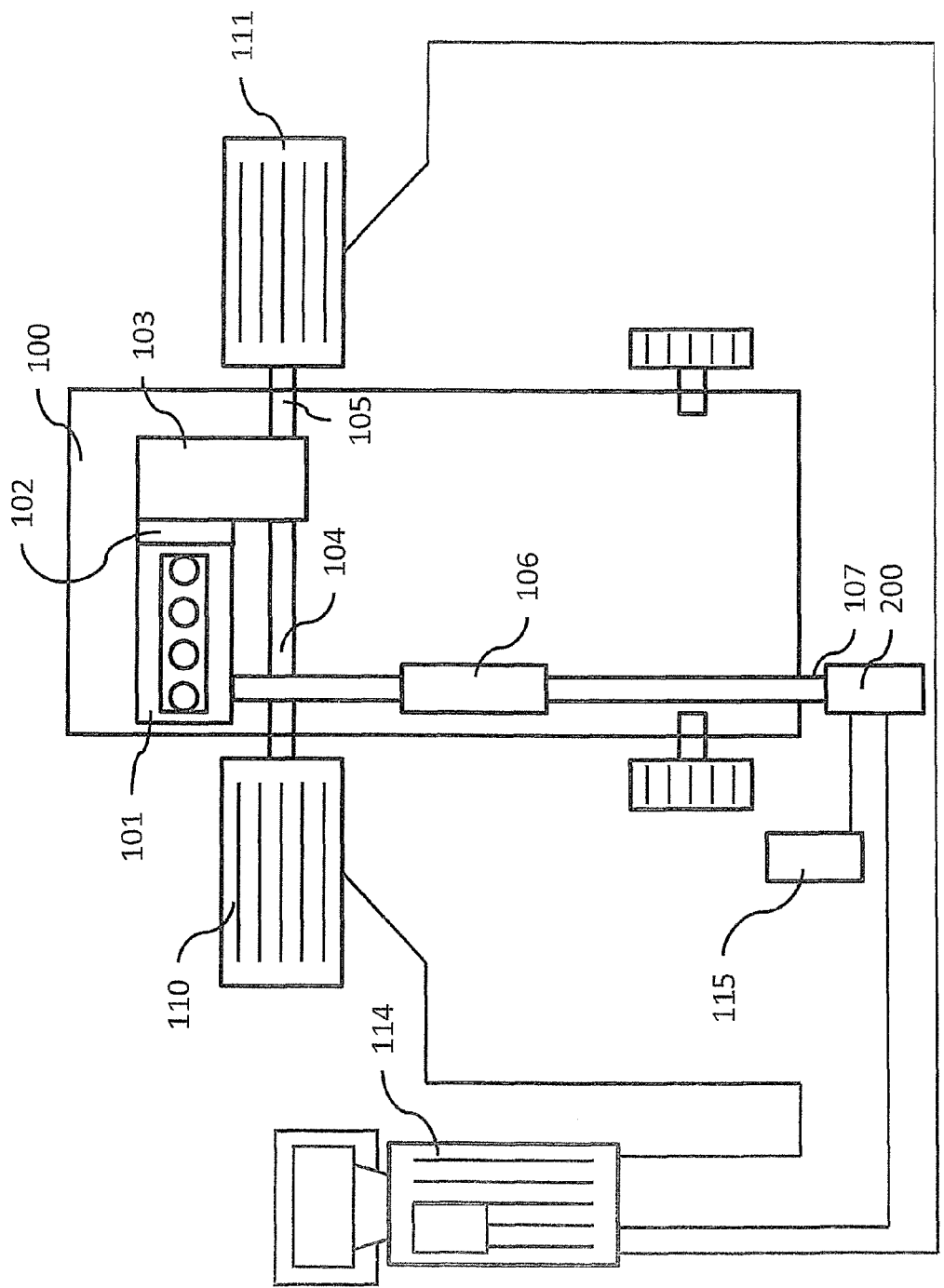
FIG. 1 schematically discloses a vehicle being tested according to the present invention.

In FIG. 1 is shown a vehicle 100 being tested according to the present invention. The vehicle 100 comprises an internal combustion engine 101 that can be selectively connected to wheel shafts 104, 105 via a clutch 102 and gear box 103. The internal combustion engine 101 is further connected to an after treatment system 106 consisting part of the vehicle exhaust system for treatment of exhaust gases resulting from combustion of fuel in the internal combustion engine 101.

For example, and as is common in vehicles today, the after treatment system 106 can include a catalytic converter for reducing one or more compounds occurring in the exhaust gas stream.

The vehicle 100 is being set up for measuring exhaust emissions and/or fuel consumption according to the present invention. The present invention provides means for performing measurements of exhaust emissions and/or fuel consumption, and in FIG. 1 the tail pipe 107 of the vehicle 100, therefore, is connected to an exemplary measurement device 200 according to the present invention.

Figure 2:
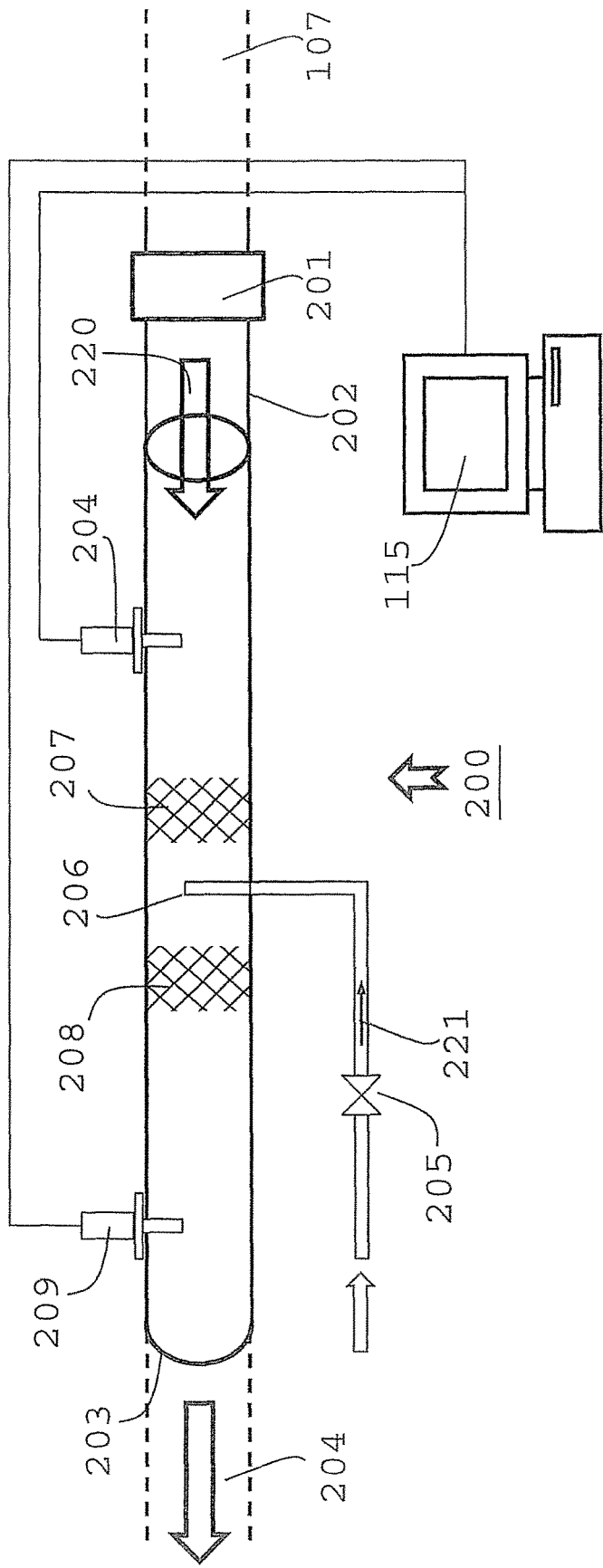
FIG. 2 schematically discloses an exemplary measurement device according to the present invention.

The measurement device 200 is shown more in detail in FIG. 2, and is connected to the vehicle 100 tail pipe 107 by means of a sealing 201 so as to ensure that at least substantially all the exhaust gases leaving the vehicle exhaust system also enters the measurement device 200.

The measurement device 200 comprises an inlet pipe 202 for connection to the vehicle tail pipe 107 by means of said sealing 201. The sealing 201 can be of any suitable kind for accomplishing an airtight seal. The measurement device 200 further comprises an outlet 203 for passage by the exhaust gas stream after measurement. If measurements are performed inside a building, the outlet 203 is preferably connected to an extraction system, schematically indicated by 204, preferably by means of an airtight sealing, for extracting the exhaust gases to the ambient outside air in a manner known per se so as to avoid exhaust gas contamination in the vehicle test/measurement premises.

An exemplary method 300 for performing a measurement according to the present invention is shown in FIG. 3. The method starts by determining if the vehicle 100 internal combustion engine 101 is started, step 301. In general, when the vehicle 100 is to be tested, the internal combustion engine 101 is started and, e.g., set to a desired working point. This can be one or more static working points or dynamically changing working points, e.g. according to a predetermined test cycle. For example, the vehicle can be connected to a chassis dynamometer comprising dynamometer test units 110, 111 being connected to the driven wheel shafts (front wheel shafts 104, 105 in this exemplary embodiment). By means of the dynamometer test units 110, 111, a desired load can be applied to the vehicle wheel shafts so as to obtain a desired load on the internal combustion engine 101. The dynamometer test units 110, 111 are connected to a common measuring and control system 114, such as e.g. a computer with associated display, by means of which the tests are controlled, and by means of which an operator of the system can initiate tests and provide necessary information for performing the dynamometer tests. Computational control of the present invention can be integrated in the measuring and control system 114, or be controlled by means of a separate control unit, such as, e.g. a control unit or computer 115 in FIG. 1. Both examples are exemplified in FIG. 1.

Examples of dynamometer test systems and methods that can advantageously be used when performing measurements according to the present invention are discloses in the following patent applications.

According to the system disclosed in FIG. 1, torque and rotational speed of measured wheel shafts can be measured in different ways, and the torque can be measured directly or indirectly, e.g. by means of a strain gauge as discussed e.g. in U.S. Pat. No. 4,669,318 or by measuring, e.g., oil pressure in a hydraulic dynamometer test unit or an electric current in a dynamometer test unit comprising an electric motor instead of hydraulic pump. The system can utilize an ultra fast control valve, such as the kind described in the international patent application WO 2004/111739 A1, by the use of which hydraulic flows and pressure can be accurately adjusted. A portion of the liquid flow can be diverted to hydraulic motors for driving e.g. a fan arrangement for cooling purposes. This is explained more in detail in WO2007/008133.

More complex testing, using a system of the above kind, is disclosed in the International patent application WO2007/133154 A1 (Engstroem).

Apart from solutions described the above patent applications, there also exist various other dynamometer test apparatuses where the present invention can be applied. In principle, the present invention can be utilised for any vehicle dynamometer.

Further, the present invention is also applicable for on-board measurements, i.e. the measurement device according to the present invention can be connected to the vehicle tail pipe, or at other suitable location in the exhaust emission system, so as to allow measurements during regular driving.

During testing, the work performed by the vehicle internal combustion engine 101 gives rise to exhaust gases resulting from the combustion of fuel in the combustion chambers such as, e.g. cylinders, of the internal combustion engine 101. The resulting exhaust gas stream passes through the after treatment system 106 where one or more compounds, such as, e.g., carbon dioxide, carbon monoxide, nitric oxides, etc. can be reduced in a manner known per se. The after treatment system 106 can comprise one or more components such as one or more catalysts, particle filters etc., and depend, e.g., on the kind of fuel being used to power the internal combustion engine 101 such as petrol, diesel, gas etc.

Further to measurement according to the present invention. As was mentioned above, instead of being dissipated into the ambient air of the vehicle at the exhaust tail pipe, the exhaust gas stream enters measurement device 200.

When the exhaust emissions gas stream 220 enters the measurement device 200, it is first subjected to a first measurement sensor 204. The sensor 204 is a sensor that measures a relative content, i.e. proportion, of a specific compound in the exhaust gas stream to be tested, step 302. That is, the sensor 204 measures the concentration, such as e.g. percentage or parts per million, PPM that the measured compound constitutes of the total exhaust gas stream.

For example, the measurement sensor 204 can be arranged to measure the concentration of e.g. oxygen, carbon dioxide or carbon monoxide in the exhaust gas stream

220. Apart from the first measurement sensor 204, the measurement device 200 can comprise two, three or any suitable number of measurement sensors, each, for example, measuring the concentration of a specific compound in the exhaust gas stream. It is also contemplated that sensors being capable of measuring the relative content of two or more compounds can be used.

However, even though the one or more measurement sensors 204 is capable of measuring the relative proportion of a compound in the exhaust gas stream 220, this measurement still does not reveal anything about the actual flow of the exhaust gas stream. For example, if the sensor 204 is, e.g., a carbon monoxide sensor, the sensor can be used to determine that the proportion of carbon monoxide is, e.g., 1% of the exhaust gas stream, but since the sensor 204 cannot measure flow, the flow can be high or low, and hence the actual emission of carbon monoxide is still completely unknown. Sensor signals from measurement sensor 204 are provided to the control unit 115 for processing according to the below. The sensor 204 is not enough to determine the total emissions of the one or more compounds in absolute values. As was mentioned above, traditional flow sensors are complicated and expensive. The measurement device 200 according to the present invention, on the other hand, allows accurate measurement of the absolute content of a compound in an exhaust gas stream using a considerably less complex and expensive solution as compared to traditional flow sensors, and without use of flow sensors for performing measurements.

When the exhaust gas stream has passed the said first sensor 204, the exhaust gas stream is, according to the embodiment described in FIG. 2, subjected to a controlled dilution, step 303. That is, a controlled flow of a defined gas such as, e.g., air is added to the exhaust gas stream downstream the first sensor 204. This is accomplished by means of an inlet 206 where, in this example, a dilution air flow 221 is added to the exhaust gas stream 220 (as is appreciated by a person skilled in the art, the supplied gas must not necessarily be air, but any suitable kind of gas can be supplied to the exhaust gas stream). That is, the gas to be supplied may contain one or more atoms constituting a component of the compound being measured by said first sensor, or the compound itself, but this is not a requirement.

Supply of the controlled flow of dilution air (gas) to be added to the exhaust gas stream can be accomplished in various ways and, for example, be accomplished by throttling pressurized air (gas). By means of a nozzle such as e.g. a critical flow nozzle 205, it can be ensured that the flow of air (or other suitable dilution gas) on the downstream side of the throttling (nozzle) 205 is always the same, and hence a known amount of gas (in this example air) can be supplied to the exhaust gas stream. A critical nozzle always discharges constant (mass) flow as long as the pressure difference exceeds a certain level. Therefore, by feeding the critical nozzle with e.g. pressurized air of high enough pressure to ensure constant mass flow according to the above, a controlled (known) amount of dilution gas can be provided to the exhaust gas stream 220.

The mass flow leaving the nozzle at the low-pressure side can easily be calculated in a manner known per se, e.g., by means of the nozzle characteristics, and where appropriate high-pressure side and low-pressure side pressures.

Consequently, by means of the pressure difference over the throttle and suitable nozzle, the amount of air (gas) being supplied to the exhaust gas stream can be set to a desired value. However, as is apparent to a person skilled in the art, there also exists various other ways to ensure that a desired flow is supplied as dilution gas flow without use of flow meters to determine the added flow. The dilution gas flow can, e.g., be entered into the control unit 115, e.g. by an operator via e.g. a keyboard or the like, or a nozzle control unit.

Combustion in internal combustion engines of different kinds of vehicles, e.g. depending on vehicle weight and/or size and kind of the combustion engine, can give rise to highly varying flows of the exhaust gas streams, and this can be accounted for according to the present invention by adjusting the amount of air (or other suitable gas) being added to the exhaust gas stream to a value that allows accurate determination of the absolute content of the first compound in accordance with the below. For example, if the added amount of air is too high, this can result in the concentration of the compound in the combination of the exhaust gas stream and the added air stream being too low to allow accurate measurement. Conversely, if the added amount of air is too low, the difference in measured concentrations can be unsatisfactory low to ensure accurate measurement results. The different flows can, for example, be accomplished by utilizing different nozzles to set a suitable flow. The flow of the dilution air stream can also be continuously controlled, e.g. by way of a variable nozzle of suitable kind (having a known characteristic) so as to allow the flow to be adapted to e.g. the flow emanating from the vehicle tail pipe.

Further, as can be seen from FIG. 2, the exhaust gas stream, prior to the addition of the dilution, but downstream of the first sensor, and also downstream of the addition of said dilution, the gas stream can be arranged to pass flow straighteners 207, 208. The flow straighteners 207, 208 are used to reduce turbulence in the gas stream, e.g. arising from the dilution air stream 221. The reduction of turbulence in the airstream can increase measurement accuracy, since the flow straighteners makes sure that the exhaust gas stream passing the location of the first measurement sensor 204, and also a second measurement sensor 209 according to the below, really has the composition that is intended to measure.

A second measurement sensor 209 is arranged downstream the inlet 206 for addition of dilution air stream, and also downstream the second flow straightener 208. The second measurement sensor 209 is preferably of the same kind or identical to the measurement sensor 204 and measures, similar to what has been described above for measurement sensor 204, a second concentration of the first compound. Sensor signals from measurement sensor 209 are also provided to the control unit 115 for processing, step 304. Consequently, by means of the first measurement sensor 204, and the second measurement sensor 209, two individual measurements of a concentration of a compound in the exhaust gas stream are obtained. Due to the addition of the dilution air stream, the relative concentration of the measured compound as measured by the second measurement sensor 209 will be different compared to the concentration obtained from the first measurement sensor 204.

This is due to the fact that the exhaust gas stream as seen from measurement sensor 209 is the combination of the exhaust gas stream emanating from the exhaust tail pipe and the dilution air stream (in general the relative concentration as measured by the second measurement sensor 209 will be lower than the concentration obtained from the first measurement sensor 204, provided that the dilution air stream does not contain a higher concentration of the measured compound than exhaust gas stream of the vehicle). As mentioned, measurement results from the first measurement sensor 204 and the second measurement sensor 209 are provided to a control system, such as control unit/computer 115, in which the measurement results are collected, and an absolute concentration of the compound is determined, step 305. The determination can, e.g. be repeated continuously or by some interval, such as 1 or more times a second, to provide a measurement of emissions over time.

Since the dilution gas volume added to the exhaust gas stream is known according to the above, the absolute content of the compound can be determined in a straight forward manner according to the following. In FIG. 5 is shown a representation of the flows and proportions (concentrations) occurring in the measurement system.

$Q_e$ represents the exhaust flow of the vehicle, e.g. in liters/second, $Q_d$ is the known dilution gas stream flow, $C_d$ is the proportion of the measured substance occurring in the dilution gas stream, this is known since dilution gas flow and kind of gas is known, if the measured substance does not occur in the dilution gas, $C_d$=0, $C_e$ is the proportion of the measured substance measured by sensor 204, $C_{de}$ is the proportion of the measured substance measured by sensor 209, and $Q_{de}$ is the combination of the exhaust gas flow and the dilution gas stream flow, i.e. $Q_d+Q_e$.

From FIG. 5, the following relation can be set up:

$$(Q_d+Q_e)C_{de}=Q_dC_d+Q_eC_e \qquad \text{(eq. 1)}$$

By means of measurement results obtained from the first and second measurement sensors 204, 209, respectively, and rewriting of eq. 1, the exhaust gas flow can then be obtained as:

$$Q_e = \frac{Q_dC_{de} - Q_dC_d}{C_e - C_{de}}, \qquad \text{(eq. 2)}$$

Consequently, by means of the two measured concentrations $C_e$, $C_{de}$, and the flow of the dilution air stream $Q_d$, the exhaust gas flow $Q_e$ resulting from combustion in the vehicle internal combustion engine 101 can be determined. Since this flow is also the flow that passes measurement sensor 204, the mass flow (absolute content) of the measured compound in the exhaust gas stream can be determined. For example, the emission of a compound, e.g. measured in grams per unit time or per travelled distance, for example as measured during dynamometer testing according to any of the above described methods or any other suitable method can be determined.

Consequently, the present invention provides an apparatus that in a simple manner is capable of measuring exhaust gas flow without use of a traditional flow sensor. Instead, relatively inexpensive chemical sensors can be used. This also means that the absolute content of a compound in the exhaust gas stream can be determined in a cost efficient manner and by means of an apparatus that can be made portable as well as economically justifiable to use in further/other areas than previously possible.

Figure 4:
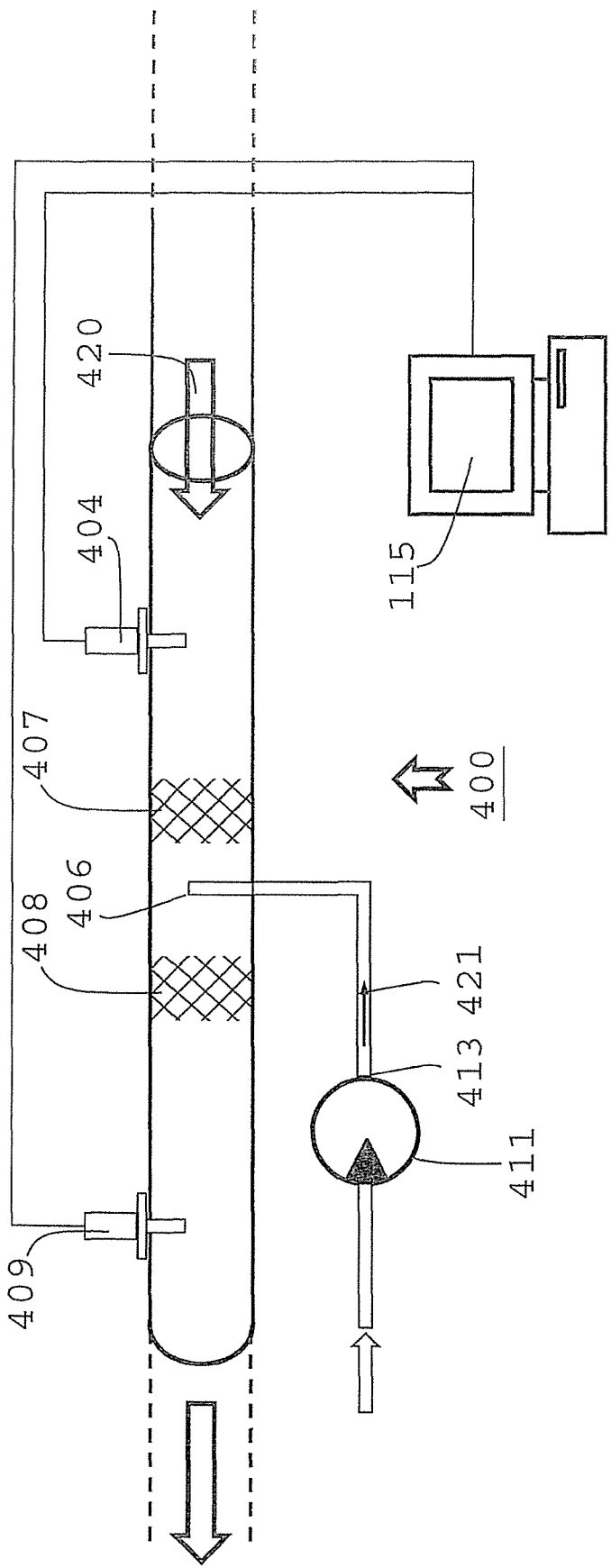
FIG. 4 schematically discloses an alternative exemplary measurement device according to the present invention.

In FIG. 4 is shown a further exemplary embodiment of the present invention. Similar to the apparatus 200 in FIG. 2, the apparatus 400 in FIG. 4 comprises a first measurement sensor 404, and first flow straightener 407. The apparatus 400 also comprises an inlet 406 for diluting the exhaust gas stream 420 with a dilution gas stream 421. However, instead of using a controlled throttling according to FIG. 2, the embodiment disclosed in FIG. 4 uses a constant volume pump 411 instead.

As can be seen from FIG. 4, the constant volume pump 411 is arranged at the location of the nozzle 205 of FIG. 2. Constant volume pumps 411 discharges a constant volume, i.e. a constant flow, at an outlet 413.

The constant volume pump 411 is preferably electrically controllable, e.g. by the control unit/computer 115 and set to discharge a volume that is suitable with respect to the flow of the exhaust gas stream. This can be ensured, for example, by increasing or decreasing the discharged flow based on measurement results (e.g. the difference between proportion measured by the first 404 and second sensor 409).

Similar to the above, the apparatus 400 also comprises second flow straightener 408 and a second measurement sensor 409 located similar to the sensor 209 of FIG. 2, and, since the constant volume pump 411 is set to discharge a constant and set volume (flow), the volume (flow) downstream of the constant volume pump will be known and the mass flow (absolute content) of a compound can be determined similar to what has been described in connection to FIG. 2.

Consequently, it has been shown different ways in which a known flow of gas can be added to the exhaust gas stream.

Naturally, there exist various other methods in which a controlled amount of dilution air (gas) can be added to the exhaust gas stream and which are included within the scope of the present invention and which can be used in accordance with the present invention.

So far, the present invention has been described in connection with the determination of the emission of a single compound in the exhaust gas stream. The present invention, however, can also be used to simultaneously, or substantially simultaneously determine the content of plural compounds in the exhaust gas stream. This can simply be accomplished by adding an additional sensor for each compound to be measured, or use sensors being capable of measuring more than one compound. Since the flow is determined by means of the pair of sensors measuring content of the first compound, it is sufficient to use a single sensor to measure the content of an additional compound. It is, however, also possible to use pairs of sensors for additional compounds, in which case the flow can be determined not only by one pair of sensors but by two pairs or more. This overdetermination can be used to increase accuracy of the determined flow and hence also the accuracy of the contents of the compounds. It can also be possible to use sensors capable of measuring the content of two or more compounds.

Further, the present invention can also be used to determine vehicle fuel consumption. Vehicles often comprise built-in fuel consumption measurement systems, but in general the accuracy of these measurement systems is poor. The present invention provides a method for accurate determination of fuel consumption. The fuel being used today is in general very well defined and well described by chemical formulas. According to the present invention, this is used to determine fuel consumption by measuring compounds in the exhaust gas stream according to the above.

The chemical reactions occurring in the combustion process in a combustion engine can, somewhat simplified, be described as:

$$C_xH_y+air \rightarrow CO_2+CO+H_2O+N_2+HC+NO_x+ \ldots \qquad \text{eq. (3)},$$

where $C_xH_y$ represents the fuel, in particular the hydrocarbons, being used. There can be various kinds of hydrocarbons in a particular kind of fuel (e.g. diesel, petrol, different octane ratings etc.), and also the composition of a particular kind of fuel, such as petrol of a particular octane rating, can vary from one provider to another. However, the compositions are in general highly defined by the providers, and it is therefore possible, with knowledge of the particular fuel being used, to replace the left hand side of eq. 3 above with the proper composition in regard of hydrocarbons and possibly the various other compounds that can occur in fuels other than hydrocarbons.

As explained above, combustion of fuel gives rise to various compounds in the exhaust gas stream. However, even though the exhaust gas stream contains various compounds, the number of carbon atoms, hydrogen atoms, etc. in the chemical reaction must be equal on both sides of equation 3.

This is utilized by the present invention for determining amount of fuel consumed by a tested vehicle. By means of sensors for measuring the relative proportion of suitable compounds in the exhaust gas stream according to the method described above, the emission of some or all of the compounds in the exhaust gas stream can be measured.

For example, in view of eq. 3, oxygen in the air supplied to the combustion process will be used for forming CO, $CO_2$, $H_2O$ and $NO_x$ in the combustion process. Similarly, the carbon will be used for forming mainly CO, $CO_2$ and HC.

The present invention can be used for measuring fuel consumption with very high accuracy by determining the emissions of several or all compounds occurring in the exhaust gas stream. Alternatively, still with high or very high accuracy, the fuel consumption can be determined using measurement of only one or a few compounds. For example, when the load of the combustion engine is low, basically all of the carbon of the hydrocarbons in the fuel will be used for generating carbon dioxide in the combustion process. The occurrence of other compounds that include carbon will occur in much lower levels, and can therefore be omitted without impact on the measurement result.

Consequently, for low motor loads, it is sufficient to determine the absolute content of carbon dioxide for low motor loads, since the number of carbon atoms provided by the fuel, and thereby amount of fuel can be determined from eq. 3 using straightforward mathematics. The present invention, therefore, also provides a simple method of determining fuel consumption of a vehicle.

In order to determine an even more accurate fuel consumption, further sensors can be used to determine the absolute content of further compounds. In general, the major part of the exhaust gas stream is composed of $CO_2$ and $N_2$. The other compounds are, in general, occurring at proportions at parts per million (ppm) levels, and hence have negligible impact on the total fuel consumption. Because of this, high accuracy in determining fuel consumption can be obtained by measuring the absolute content of more than one but still only a few compounds. With regard to CO, this compound can be high at high motor load levels, and hence it can be advantageous, at least for some measurements, to include CO measurements in the determination of fuel consumption.

Instead of using carbon atoms for determining fuel consumption, it is also possible to use oxygen atom analysis when determining fuel consumption. As is shown in eq. 3, the combustion process is mainly a process including hydrocarbons and oxygen (and heat), and with proper knowledge of the amount of oxygen (air) supplied to the combustion process the determination of fuel consumption can be performed using oxygen analysis as well. In one embodiment, both carbon atom analysis and oxygen atom analysis is performed.

In the above description, a particular kind of dynamometer test unit have been described, but as has been explained, the present invention is applicable for use when testing vehicles by any kind of dynamometer test units, or during actual driving.

Further, so far the present invention has been described in connection with measurements of emissions from a vehicle. The present invention, however, is equally applicable for measuring emissions from any kind of internal combustion process, such as, e.g. emissions from any kind of plant or moving object such as boat ship etc. were emission measurements or exhaust gas flows and/or fuel consumption is of interest. As has been disclosed above, the present invention can also be utilized to measure the exhaust gas flow, and according to one embodiment only this flow is determined, and not the mass flow of a compound.

According to a further embodiment of the invention, the device according to the invention is integrated in a vehicle exhaust system.

The invention claimed is:

1. Method for measuring at least one compound in an exhaust gas stream resulting from internal combustion, said method including:
   measuring a first relative proportion of oxygen in the exhaust gas stream, using a first oxygen sensor,
   adding a defined flow of air to said exhaust gas stream downstream of said first oxygen sensor,
   measuring a second relative proportion of oxygen in a combined stream of said exhaust gas stream and said added gas, using a second oxygen sensor, and
   determining a mass flow of oxygen in said exhaust gas stream resulting from said combustion in said internal combustion based upon said first and second relative proportions and based upon said defined flow of air, and
   adjusting said defined flow of air being added to the exhaust gas stream based upon said determined mass flow of oxygen in said exhaust gas stream.

2. Method according to claim 1, further including:
   continuously or at intervals determining mass flow of oxygen in said exhaust gas stream flow, so as to continuously or at intervals determine emission of oxygen in said exhaust gas stream.

3. Method according to claim 1, wherein said first flow is at least partially set based on the flow of said exhaust gas stream.

4. Method according to claim 1, wherein said defined flow is input to a control unit or computer performing said determination of said mass flow of oxygen in said exhaust gas stream.

5. Method according to claim 1, wherein said defined flow of air is set by means of a controllable throttling.

6. Method according to claim 1, further including:
   measuring a first relative proportion of a second compound in the exhaust gas stream using said first oxygen sensor or a third sensor, and
   measuring a second relative proportion of said second compound in the combined stream of said exhaust gas stream and said added gas, using said second oxygen sensor or a fourth sensor, and
   determining a mass flow of said second compound in said exhaust gas stream resulting from said combustion in said internal combustion based upon said first and second relative proportions of said second compound and based upon said defined flow of air.

7. Method according to claim 1, further comprising:
determining fuel consumption of said combustion by said at least one mass flow of at least one compound.

8. Method according to claim 1, wherein said measurements are performed by a measurement device connected to a vehicle exhaust system.

9. Method according to claim 1, wherein said measurements are performed by a measurement device connected to a vehicle exhaust system tail pipe.

10. Method according to claim 1, further comprising:
increasing said defined flow of air when it is determined that the concentration of oxygen in the combined stream of said exhaust gas stream and said added gas is lower than a first value.

11. Method according to claim 1, further comprising:
decreasing said defined flow of air when it is determined that the concentration of oxygen in the combined stream of said exhaust gas stream and said added gas exceeds a second value.

12. Method according to claim 1, further comprising:
continuously or at predetermined intervals adjusting said defined flow of air being added to the exhaust gas stream based on said determination of the mass flow of oxygen.

13. Method according to claim 1, further comprising
determining the flow of said combined stream ($Q_e$) of said exhaust gas stream and said added gas as:

$$Q_e = \frac{Q_d C_{de} - Q_d C_d}{C_e - C_{de}},$$

where $Q_d$, is said defined flow of air, $C_d$ is the proportion of oxygen occurring in air, $C_e$ is said first relative proportion of oxygen, and $C_{de}$ is said second relative proportion of oxygen, and determining said mass flow of oxygen by means of said flow of said combined stream ($Q_e$) and said second relative proportion of oxygen.

14. Method according to claim 1, further including:
drawing a controllable flow of air using a suction device, said controllable flow being said defined flow of air, said controllable flow being discharged into said exhaust gas stream.

15. Method according to claim 14, where said suction device is arranged to discharge a constant flow.

16. Method according to claim 14, wherein said suction device comprises a constant volume pump.

17. Method according to claim 1, wherein said internal combustion is internal combustion in an internal combustion engine.

18. Method according to claim 17, wherein said measurements are performed for a plurality of engine loads.

19. Computer program product, which when run on a control unit or a computer integrated in or connected to a measurement device, causes the control unit or computer to execute the method according to claim 1.

20. Computer program product according to claim 19, wherein the computer program product comprises a computer readable medium.

21. Method for measuring an exhaust gas stream resulting from internal combustion, said method including:
measuring a first relative proportion of oxygen in the exhaust gas stream, using a first oxygen sensor,
downstream of said first oxygen sensor, adding a defined flow of air to said exhaust gas stream,
measuring a second relative proportion of oxygen in a combined stream of said exhaust gas stream and said added gas, using a second oxygen sensor, and
determining a flow ($Q_e$) of said exhaust gas stream resulting from said combustion in said internal combustion based upon said first and second relative proportions and said defined flow of air, and
adjusting said defined flow of air being added to the exhaust gas stream based upon said determined mass flow of oxygen in said exhaust gas stream.

22. Method according to claim 21, further comprising:
determining said flow ($Q_e$) as:

$$Q_e = \frac{Q_d C_{de} - Q_d C_d}{C_e - C_{de}},$$

where $Q_d$ is said defined flow of air, $C_d$ is the proportion of oxygen occurring in air, $C_e$ is said first relative proportion of oxygen, and $C_{de}$ is said second relative proportion of oxygen.

23. System for measuring at least one compound in an exhaust gas stream resulting from internal combustion, said system including:
a first oxygen sensor for measuring a first relative proportion of oxygen in the exhaust gas stream,
a device for adding a defined flow of air to said exhaust gas stream downstream said first oxygen sensor,
a second oxygen sensor for measuring a second relative proportion of oxygen in a combined stream of said exhaust gas stream and said added gas, and
a control unit or computer for determining a mass flow of oxygen in said exhaust gas stream resulting from said combustion in said internal combustion by means of said first and second relative proportions and said defined flow of air, and
a control unit for adjusting said defined flow of air being added to the exhaust gas stream based upon said determined mass flow of oxygen in said exhaust gas stream.

24. System according to claim 23, further comprising a device for variably adjusting said defined first flow.

25. Vehicle dynamometer, comprising a system according to claim 23.

* * * * *